United States Patent [19]

Durand et al.

[11] 4,290,428
[45] Sep. 22, 1981

[54] CATHETER WITH BULB

[76] Inventors: Alain J. M. Durand, 12, Rue Jean-Jaures, F-95600 Eaubonne; Jean C. Farcot, 18, Parc du Bearn, F-92210 Saint-Cloud, both of France

[21] Appl. No.: 67,161

[22] Filed: Aug. 16, 1979

[30] Foreign Application Priority Data

Sep. 1, 1978 [FR] France ................... 78 25254

[51] Int. Cl.³ ............................................ A61M 16/00
[52] U.S. Cl. ................................................. 128/349 B
[58] Field of Search ............ 128/349 B, 349 BV, 344, 128/246, 129

[56] References Cited

U.S. PATENT DOCUMENTS

| 3,707,151 | 12/1972 | Jackson | 128/349 B |
| 3,788,326 | 1/1974 | Jacobs | 128/349 B |
| 4,090,518 | 5/1978 | Elam | 128/349 B |
| 4,091,816 | 5/1978 | Elam | 128/349 B |

Primary Examiner—Bradley Garris
Attorney, Agent, or Firm—Michael J. Striker

[57] ABSTRACT

This catheter for blood retroperfusion comprises a tube and a flexible bulb through which the tube passes; ports are formed in the tube portion surrounded by the bulb, and their total surface area is at least equal to the total surface area of the fluid passage of the tube between the latter and the cavity into which the catheter is introduced in actual use.

2 Claims, 4 Drawing Figures

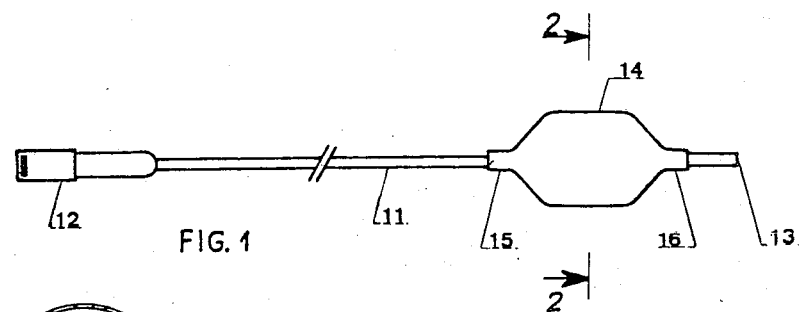
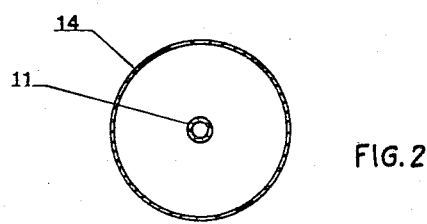
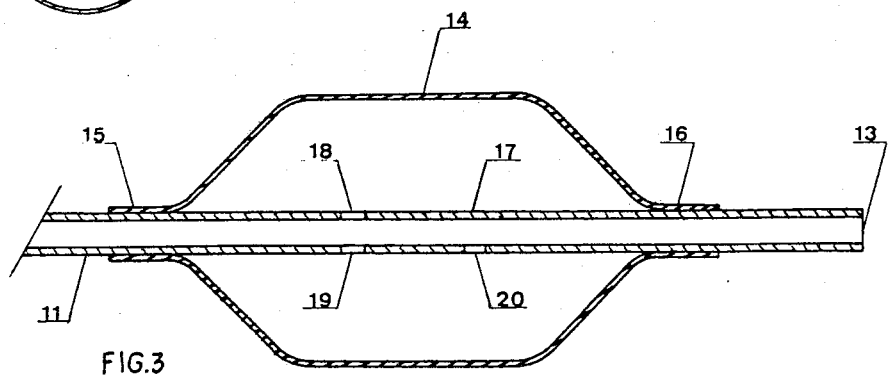
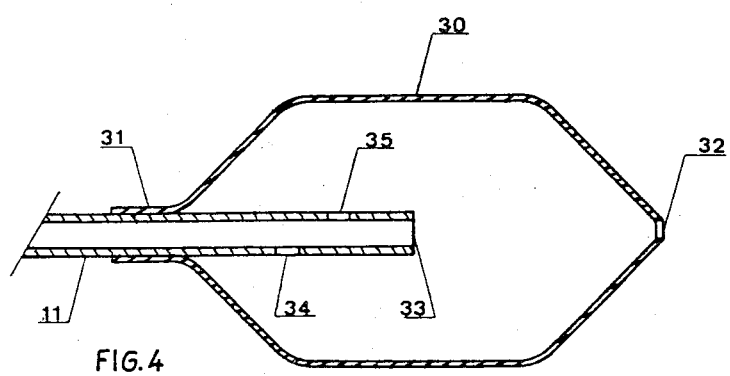

CATHETER WITH BULB

BACKGROUND OF THE INVENTION

1. Field of the Invention

This invention relates in general to catheters intended for use in the practice of medical or veterinarian art, and has specific reference to a catheter with bulb, designed for combating by retroperfusion the consequences of coronary diseases.

2. Reference to the Prior Art

To obtain a retroperfusion, the conventional method consists in utilizing a catheter of which the tube has at least two orifices formed therein, the distal end of the tube being provided with a rubber bulb.

One orifice is used for transferring the liquid or gas in order to inflate and deflate the bulb, and the other orifice is used for injecting blood under counter-current conditions.

However, the use of a catheter of this character requires an extremely complicated apparatus in order to obtain a satisfactory synchronization between the bulb pulsations and the fluxes of perfused blood, with due consideration, of course, for the patient's cardiac pulsations. On the other hand, the presence of at least two orifices in the catheter tube implies that the outer diameter of this tube be relatively large in order to produce a sufficient output during the retroperfusion.

SUMMARY OF THE INVENTION

It is the primary object of this invention to avoid these inconveniences.

The catheter according to this invention for performing blood retroperfusions comprises a bulb non-detachably secured to the tube extending completely through the bulb, this tube being provided with a fluid passage opening directly into the bulb and into the cavity receiving the catheter end. According to this invention, the total surface area of the fluid passage ports between the tube fluid passage and the inner space of the bulb is at least equal to the total surface area of the fluid passage orifices between the tube fluid passage and the cavity into which the catheter end is introduced.

In the foregoing and in the following disclosure, the term "tube fluid passage" designates the free inner volume of the tube through which the fluid is caused to flow. This passage is used both for inflating the bulb and for transferring liquid into the catheterized blood-vessel.

The lateral orifices or ports formed through the tube wall, of which the total cross-sectional area is at least equal to the cross-sectional area of the tube fluid passage of the catheter, permit of automatically inflating and deflating the bulb during the afflux or reflux of blood in the tube fluid passage of the catheter. In a modified form of embodiment of the invention, the bulb is secured to the distal end of the tube of which is constitutes somewhat the extension. The blood flux from the tube begins to fill up the bulb before escaping through the distal orifice of the bulb, the cross-sectional surface area of this distal orifice being at the most equal to the surface area of the distal orifice of the tube. In another modified version the tube end opens into the bulb and comprises lateral ports opening likewise into the bulb. In this case, the total cross-sectional surface area of the lateral ports and of the distal orifice of the tube must be at least equal to the surface area of the distal orifice of the bulb.

BRIEF DESCRIPTION OF THE DRAWING

FIG. 1 is a side elevational view of a catheter according to this invention, shown with the bulb in its inflated condition.

FIG. 2 is a cross section taken along the line 2—2 of FIG. 1.

FIG. 3 is an axial section showing the same catheter of which the tube extends through the bulb, and FIG. 4 is an axial section showing a modified form of embodiment of the catheter of this invention, in which the tube opens into the bulb.

DESCRIPTION OF THE PREFERRED EMBODIMENTS

Referring to FIG. 1, the tube 11 of the catheter has its proximal end provided with a standard, Luer-type female union 12 having a 6% cone taper, for connecting syringes or inserts of any suitable and known perfusion apparatus. The free internal volume or fluid passage of this tube terminates at 13 with a normally rounded edge to avoid any injury to the patient's vessel. A rubber or like bulb 14 is fitted on the tube 11 and secured thereto at points 15 and 16. Thus, the central tube 11 is surrounded by the wall 14 of the inflated bulb (see FIG. 2).

According to the invention, the portion of the tube 11, which is surrounded by the bulb 14, is provided with lateral ports 18, 19 and 20 of which the total surface area is at least equal to the surface area of the outlet end 13 of said tube 11 (see FIG. 3).

The principle of operation of the catheter according to this invention will be clearly understood if reference is made to FIG. 3. When a flux of liquid under pressure, introduced into the fluid passage of the catheter, flows across the lateral ports 18 and 19, one fraction of this liquid will escape into the bulb so as to inflate same immediately. During the extremely short time period necessary for inflating the bulb, the liquid flux issuing from the outlet orifice 13 is of course extremely moderate, but when the bulb is filled completely, a maximum output is resumed through the outlet orifice 13.

In the second phase of operation of the catheter, when the liquid is sucked in through the proximal union 12, the resistance counteracting the free flow of fluid through the lateral ports 18, 19 and 20 is lower than the resistance produced by the outlet orifice 13, so that the bulb 14 will firstly deflate very rapidly while the output through orifice 13 is low, and then, when the bulb is deflated and its wall 14 contacts the tube 11, the liquid withdrawal is complete, without any braking interference.

In FIG. 4, the principle of operation of the catheter of this invention is obviously unchanged: the total surface area corresponding to the distal orifice 33 and the lateral ports 34 and 35, of which the number may vary from 0 to 20 according to requirements, is at least equal to the surface area of the bulb orifice 32, and it is always the bulb that reacts first and completely to a liquid afflux or suction.

Besides, practical tests proved that the operation of the device is facilitated when the distance between the orifices 33 and 32 is relatively reduced, for example of the order of one to ten times the diameter of tube 11. On the other hand, no appreciable difference has been observed in the operation of the device according to the specific positions of the lateral ports 34 and 35, or according to their number, for only their total surface area could produce a difference. However, it may be assumed that using the catheter with blood leads to reduce the number of these lateral ports and even to dispense therewith in order to minimize possible changes in the blood structure in case of rapid flow through these lateral ports having necessarily a reduced diameter.

A simple method of manufacturing this catheter consists in selecting a tube of thermoplastic elastomer or polymer, such as PVC, polyamid or polyurethane, having an outer diameter of 0.5 to 5 mm, and to manufacture separately a bulb or ballonet of a diameter ranging from 0.5 to 40 mm either from materials pertaining to the same group but specially selected for their inherent elasticity, or from latex, and then assembling the tube and the bulb in the selected position. This last step is simply a cementing or welding operation, with or without using reinforcing binding means such as ligatures according to techniques well known in the art.

Of course, this invention should not be construed as being strictly limited by the specific forms of embodiment illustrated and described herein, since many modifications and changes may occur to those skilled in the art, according to the specific applications contemplated, without departing inasmuch from the basic principles of the invention as set forth in the appended claims. Thus, changes may be brought in the catheter tube according to this invention in connection with the diameters, curvature, the use of stiffeners, miscellaneous mandrel types, as a function of the vessels and cavities for which they are intended. The lateral ports formed through the tube wall may have a round or other configuration, and their disposition on the tube portion lying inside the bulb is immaterial; the number of these ports, as already mentioned hereinabove, may range from 0 to 20.

When introduced into a vessel (notably an arterial or venous vessel) the catheter according to this invention is capable of producing the following actions reliably and reproducibly in time: inflating the bulb and stopping the natural flow in the vessel; reversing the natural direction of flow of the blood; making a retroperfusion; producing a rapid deflation of the bulb, and finally resuming a natural flow.

The catheter of this invention is also applicable to many cases such as the systematic X-ray explorations of human or animal vessels or cavities.

What is claimed as new is:

1. A catheter for blood retroperfusion, which comprises a tube of which the inner fluid passage opens directly into a bulb secured non-detachably to said tube, said bulb further comprising an orifice communicating with the cavity into which the catheter is introduced in actual use, wherein the total surface area of the communication ports between said tube fluid passage and the inner space of said bulb is at least equal to the total surface area of the orifice permitting the communication between the inner space of said bulb and the cavity into which the catheter is introduced.

2. The catheter of claim 1, wherein said bulb is of elastomeric material.

* * * * *